(12) United States Patent
Radicke et al.

(10) Patent No.: US 11,259,783 B2
(45) Date of Patent: Mar. 1, 2022

(54) DETERMINING A REGION OF INTEREST TO BE RENDERED

(71) Applicant: Siemens Healthcare GmbH, Erlangen (DE)

(72) Inventors: Marcus Radicke, Veitsbronn (DE); Ludwig Ritschl, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 399 days.

(21) Appl. No.: 16/519,306

(22) Filed: Jul. 23, 2019

(65) Prior Publication Data

US 2020/0029938 A1 Jan. 30, 2020

(30) Foreign Application Priority Data

Jul. 26, 2018 (EP) .................................... 18185658

(51) Int. Cl.
| | | |
|---|---|---|
| *A61B 8/08* | (2006.01) | |
| *A61B 8/00* | (2006.01) | |
| *A61B 6/00* | (2006.01) | |

(52) U.S. Cl.
CPC .......... *A61B 8/5207* (2013.01); *A61B 6/4417* (2013.01); *A61B 6/502* (2013.01); *A61B 6/5205* (2013.01); *A61B 8/0825* (2013.01); *A61B 8/4416* (2013.01)

(58) Field of Classification Search
CPC ... A61B 8/4416; A61B 8/5207; A61B 6/4417; A61B 6/5205
See application file for complete search history.

(56) References Cited

U.S. PATENT DOCUMENTS

| | | | |
|---|---|---|---|
| 6,421,454 B1* | 7/2002 | Burke ................. | A61B 8/4416 382/131 |
| 2017/0251991 A1 | 9/2017 | Wang et al. | |
| 2018/0174294 A1 | 6/2018 | Palma et al. | |

FOREIGN PATENT DOCUMENTS

| | | | |
|---|---|---|---|
| EP | 3336803 A1 | 6/2013 | |
| EP | 3219261 A1 | 9/2017 | |

OTHER PUBLICATIONS

European Office Action dated Oct. 1, 2021.
Benedikt Schaefgen et al.: "Initial results of the FUSION-X-US prototype combining 3D automated breast tomosynthesis"; European Radiology; 8d. 28; Nr. 6;. pp. 2499-2506; XP055537415; DE; ISSN: 0938-7 994; DOI: 10.1007/s00330-017-5235-8; 2018.
European Search Report with Application No. 18185658.4 dated Jan. 7, 2019.

* cited by examiner

*Primary Examiner* — Boniface Ngathi
*Assistant Examiner* — Boniface N Nganga
(74) *Attorney, Agent, or Firm* — Harness, Dickey & Pierce P.L.C.

(57) ABSTRACT

An embodiment is for determining a region of interest to be rendered in an ultrasound volume data set of an interior of an object under examination. In an embodiment, the method includes: determining a projection position in a two dimensional X-ray projection image of the object under examination, wherein a projection ray correlated to the projection position passes through the region of interest; and extracting a partial data set encompassed by the ultrasound volume data set using the projection position determined and based upon geometrical information relating to the X-ray 3D ultrasound unit.

21 Claims, 4 Drawing Sheets

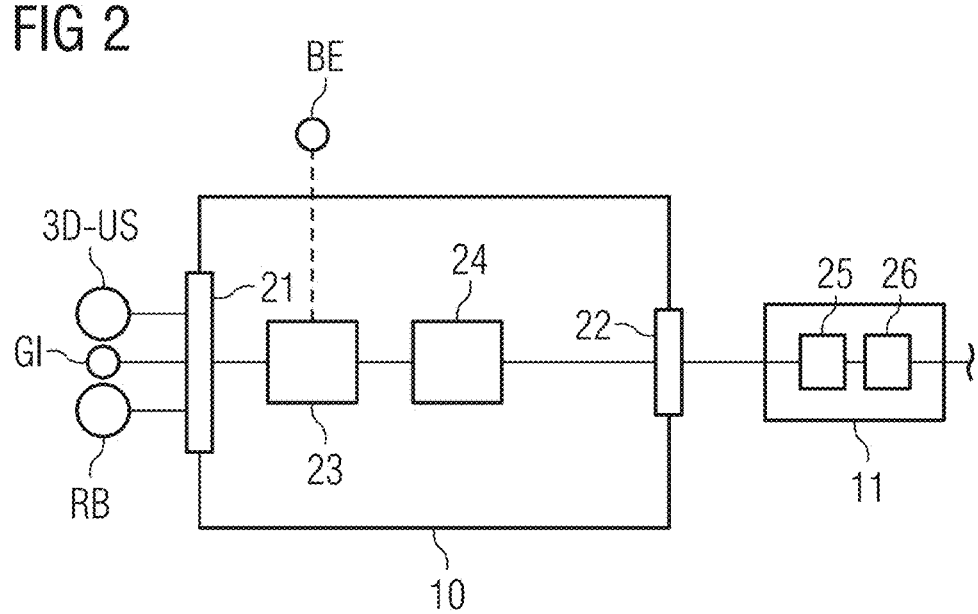
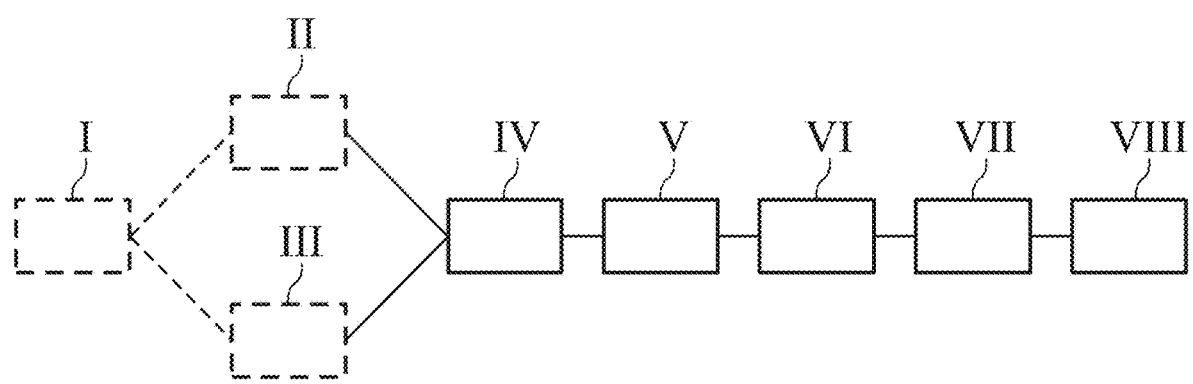

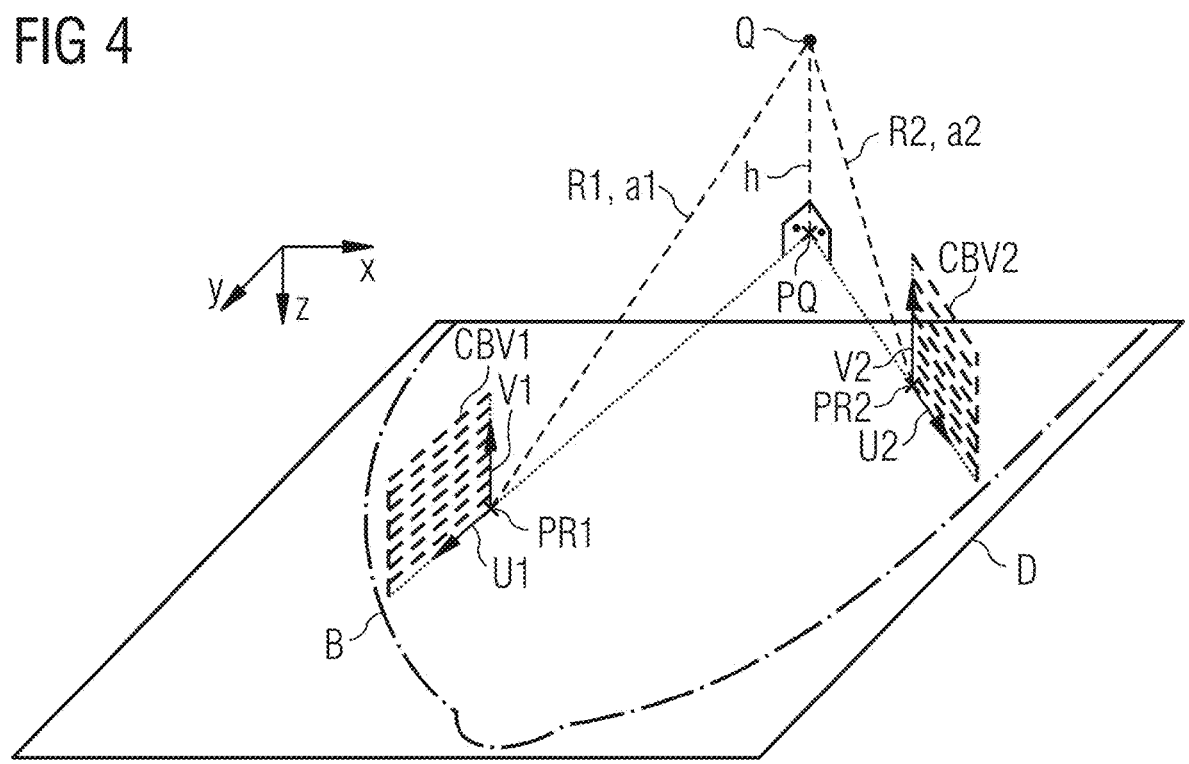

DETERMINING A REGION OF INTEREST TO BE RENDERED

PRIORITY STATEMENT

The present application hereby claims priority under 35 U.S.C. § 119 to European patent application number EP 18185658.4 filed Jul. 26, 2018, the entire contents of each of which are hereby incorporated herein by reference.

FIELD

Embodiments of the invention generally relate to a method for determining a region of interest to be rendered, a method for rendering a region of interest, an image processing device and an X-ray system.

BACKGROUND

Medical examinations of a breast, particularly those of a human female breast, are generally carried out to identify or rather diagnose malignant changes in the breast tissue in a targeted and reliable manner. Mammography is a commonly used method of carrying out such an examination.

For a mammographic examination, the breast is positioned and compressed between two compression plates in an X-ray apparatus, or more specifically a mammography unit, and in this state an X-ray image is generated. For this purpose X-rays are emitted from an X-ray source. As they pass through the breast, these rays are attenuated in their intensity according to the nature and structure of the tissue penetrated and are then picked up by a detector to produce a mammogram.

Depending on the diagnostic findings or tissue property of the breast under examination, it may be advantageous to also determine additional or supplementary information relating to the breast tissue being examined. In practice, a volume image of the breast is therefore often acquired via tomosynthesis or ultrasound. However, a disadvantage of tomosynthesis is that the patient is exposed to an increased radiation dose.

In the case of an ultrasound or sonography scan, ultrasound waves are emitted by an ultrasound probe in the direction of an object to be examined, such as the breast of a female patient. The ultrasound waves are scattered, refracted and reflected from different structures of the target object. The returning ultrasound waves are received again by the ultrasound probe and then evaluated and converted to enable an image of the interior of the target object to be generated. This rendering can be both 2-dimensional and 3-dimensional.

In order to usefully link the different technologies, ultrasound and X-ray mammography, and make diagnostic assessment as simple as possible, combination units are used in practice. In a combined X-ray/3D ultrasound unit of this kind (hereinafter referred to as an XUS unit for short) an ultrasound probe of the ultrasound arrangement is generally disposed between the X-ray source and the detector of the X-ray unit. It can basically be disposed both on the side of the target object facing the detector and on the side of the target object facing the X-ray source. The ultrasound probe, the detector and the compression plates are generally disposed parallel to one another. By way of this arrangement, scans providing essentially similar views of the object under examination can therefore be produced using the two different imaging methods.

However, it is difficult to establish a local correlation between the two dimensional X-ray image (mammogram) and a position in a three-dimensional ultrasound image or ultrasound volume data set. For example, if a diagnostician has detected in the X-ray image a position which lies within a region of interest, an unambiguous correlation of the position with a corresponding position in the ultrasound image is not possible. This is because the spatial information is lacking due to the inherent property of a projection image. Another difficulty is that the X-ray beam path is cone-shaped. As a result, it is difficult to establish a correlation between a position in the X-ray projection image, or a pixel of the X-ray detector, and the elements in the three-dimensional ultrasound image which correspond to the structures of the object under examination that lie on a perpendicular to the detector surface passing through the pixel.

In order to determine the position more precisely, in practice a second X-ray projection image is acquired at a defined angle with respect to the first X-ray projection image. This enables an accurate position relative to the XUS unit and therefore also in the three-dimensional ultrasound image to be determined. However, this is disadvantageous for the patient because of the increased radiation exposure.

Transformation of the coordinate system of the ultrasound volume data set is basically also possible. For this purpose the ultrasound volume data set is transformed using standard methods of transformation and interpolation into the conical geometry of the X-ray beam path. The ultrasound volume data set then correlates with the X-ray projection image, so that visualization is readily possible.

SUMMARY

However, the inventors discovered that after the transformation, the ultrasound volume data set is present in a distorted image, making correct diagnostic assessment impossible or at least much more difficult.

At least one embodiment of the present invention is directed to indicating a local correlation between a two dimensional X-ray projection image and an ultrasound volume data set and allow a good diagnostic assessment while minimizing the radiation dose.

Embodiments are directed to a method for determining a region of interest, a method for rendering a region of interest, an image processing device, and an X-ray system.

An embodiment of the method, for determining a region of interest to be rendered in an ultrasound volume data set of the interior of an object under examination acquired via an X-ray 3D ultrasound unit, comprises at least the following.

determining a projection position in an, in particular, single two dimensional X-ray projection image of the object under examination, wherein a projection ray correlated to the projection position passes through the region of interest; and extracting a partial data set encompassed by the ultrasound volume data set using the projection position and on the basis of geometrical information relating to the mammography 3D ultrasound unit.

An embodiment is directed to an image processing device incorporating all the components for carrying out one of the above described methods according to embodiments of the invention.

The image processing device can basically operate independently of the modalities required for acquisition. It can therefore be inventively used, for example, to also process data of separate X-ray and ultrasound equipment. Thus, for example, the location of a probe of the ultrasound device relative to the object under examination and/or X-ray unit can be determined/tracked by sensors using known methods. This also enables the relative location of the X-ray projection image and the three-dimensional ultrasound data set to be determined.

An embodiment is directed to an X-ray system comprising an inventive image processing device of at least one embodiment and an X-ray 3D ultrasound unit. The latter comprises a source-detector arrangement which is designed to acquire an X-ray projection image of an object under examination. The XUS unit also comprises an ultrasound arrangement which is designed to acquire an ultrasound volume data set. The XUS unit is preferably a mammography unit having an additional ultrasound arrangement as compared to standard mammography units.

The image processing device according to at least one embodiment of the invention can be advantageously retrofitted to existing X-ray systems. However, it is also possible to equip new X-ray systems with an image processing device according to at least one embodiment of the invention as early as the manufacturing stage thereof.

At least one embodiment is directed to a method for determining a region of interest to be rendered in an ultrasound volume data set of an interior of an object under examination, the method comprising:

determining a projection position in a two dimensional X-ray projection image of the object under examination, wherein a projection ray correlated to the projection position passes through the region of interest; and extracting a partial data set encompassed by the ultrasound volume data set using the projection position determined and based upon geometrical information relating to the X-ray 3D ultrasound unit.

At least one embodiment is directed to a method for rendering a region of interest, comprising:

providing a number of views from a partial data set determined according to the method of an embodiment; and rendering at least one view of the number of views provided.

At least one embodiment is directed to an image processing device for determining a region of interest to be rendered in an ultrasound volume data set of an inside of an object under examination, the data set having been acquired via an X-ray 3D ultrasound unit, the image processing device comprising:

at least one processor to determine a projection position in a two dimensional X-ray projection image of the object under examination, wherein a projection ray correlated to the projection position passes through the region of interest and extract a partial data set from the ultrasound volume data set using the projection position determined and based upon geometrical information relating to the X-ray 3D ultrasound unit.

At least one embodiment is directed to an X-ray system, comprising:

the image processing device of an embodiment; and an X-ray 3D ultrasound unit including a source-detector arrangement designed to obtain an X-ray projection image of an object under examination, and an ultrasound arrangement designed to acquire an ultrasound volume data set.

At least one embodiment is directed to a non-transitory computer program product storing a computer program, directly loadable into a storage device of an image processing device, including program sections for carrying out the method of an embodiment when the computer program is executed in the image processing device.

At least one embodiment is directed to a non-transitory computer-readable medium storing program sections readable and executable by a processor to carry out the method of an embodiment when the program sections are executed by the processor.

An advantage of a largely software-based implementation is that even image processing equipment already in use can be easily upgraded by a software update in order to operate in the manner according to an embodiment of the invention. In this respect, at least one embodiment is directed to a corresponding computer program product comprising a computer program which can be loaded directly into a storage device of an image processing device of an X-ray system, having program sections for carrying out all the steps of the method according to an embodiment of the invention when the program is executed in the image processing device. As well as the computer program, such a computer program product can possibly comprise additional elements such as e.g. a documentation and/or additional components, including hardware components such as e.g. a hardware key (dongles, etc.) for using the software.

BRIEF DESCRIPTION OF THE DRAWINGS

The invention will now be explained once again in greater detail with reference to the accompanying drawings using example embodiments. The same components are provided with identical reference characters in the different figures. In the figures, which are generally not to scale:

FIG. 2 shows a schematic block diagram of an example embodiment of an image processing device according to the invention comprising a rendering device, FIG. 3 shows a schematic block diagram for the sequence of an example embodiment of a method according to the invention for determining and rendering a region of interest, FIG. 4 shows a schematic perspective view of the extraction of a partial data set according to a first example embodiment of a method according to the invention for determining a region of interest to be rendered.

DETAILED DESCRIPTION OF THE EXAMPLE EMBODIMENTS

Figure 1:
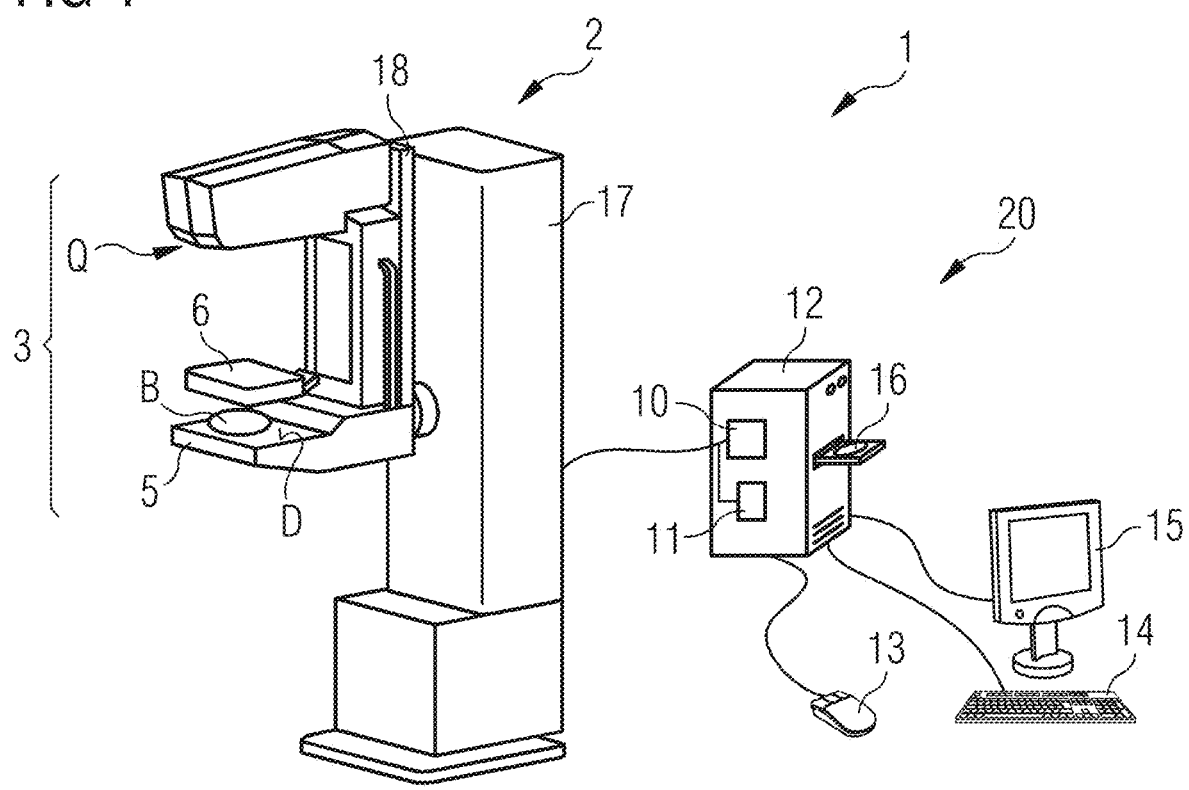
FIG. 1 shows a grossly schematic representation of an example embodiment of an X-ray system according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the method, for determining a region of interest to be rendered in an ultrasound volume data set of the interior of an object under examination acquired via an X-ray 3D ultrasound unit, comprises at least the following.

determining a projection position in an, in particular, single two dimensional X-ray projection image of the object under examination, wherein a projection ray correlated to the projection position passes through the region of interest; and extracting a partial data set encompassed by the ultrasound volume data set using the projection position and on the basis of geometrical information relating to the mammography 3D ultrasound unit.

The object under examination can basically be any object to be examined using X-ray and ultrasound. However, it is preferably the breast of a human female patient. The region of interest to be rendered is a region which is to be particularly taken into account as part of an examination or diagnostic assessment. This can be lesions, microcalcifications, lumps or the like.

The data, i.e. the X-ray projection image and the ultrasound volume data set, is acquired before the start of the actual method according to the invention, in particular using an X-ray 3D ultrasound unit (XUS unit). This is a combination unit with which both X-ray images and ultrasound scans of the object under examination can be produced. It therefore preferably comprises an X-ray source and an X-ray detector as well as an ultrasound probe which is designed to emit ultrasound waves and detect reflections thereof from the object under examination. The XUS unit is therefore, in accordance with the object under examination, a combined ultrasound-mammography unit.

For example, in a preparatory step preceding the method according to the invention, the XUS unit can be used to acquire both the two dimensional X-ray projection image and the three-dimensional ultrasound volume data set.

However, the X-ray projection image and/or the ultrasound volume data set can also have been stored in a storage device, for example, and retrieved therefrom to carry out the method according to an embodiment of the invention. The X-ray projection image is preferably a mammogram.

A projection position is basically understood as being a position in the X-ray projection image, i.e. an image spot, for example, preferably corresponding to a pixel of an X-ray detector. The projection position is preferably located in the region of interest, with particular preference centrally therein. The projection position can be determined by a user input and/or via a computer algorithm (computer aided detection—CAD), as will be explained in greater detail below. The projection position is determined in particular in a single X-ray projection image, as this enables the radiation dose for the patient to be advantageously minimized.

The projection ray constitutes a connecting line between the projection position, or rather a detector pixel correlated thereto, and the X-ray source, i.e. the X-ray focus. The X-ray source has in particular a cone beam geometry. Particularly in edge regions of the detector, this results in angles of incidence that are oblique, i.e. deviating from the perpendicular. Disregarding scattered radiation effects, the pixel or image point therefore reproduces, at the projection position, as a pixel value or brightness, accumulated or integrated information about the ROI tissue that has been penetrated along the projection ray.

In order to be able to completely visualize this information also in the three-dimensional ultrasound volume data set without using the entire ultrasound volume data set, part of the data is selected and a partial data set is generated therefrom, i.e. extracted. This is carried out on the basis of the projection position. That is to say, the data is selected according to an association or correlation between the projection position and at least some of the data of the ultrasound volume data set corresponding to the projection position, i.e. information about the same region of the object under examination as that encompassed by the image point of the projection position. The partial data is preferably a small portion of the data of the ultrasound volume data set, i.e. less than 20%, preferably less than 10%, for example, so that a diagnostician is able to create a detailed picture of the region of interest as quickly as possible.

In addition, geometrical information or rather position information relating to the mammography 3D ultrasound unit is used for extraction of the partial data set. This is in particular a relative position, i.e. a position in the translational degrees of freedom and/or orientation in the rotational degrees of freedom, between the X-ray source and detector, i.e. also between the X-ray source and the pixel of the detector or rather the image point in the X-ray projection image. This information can be used to trace the path of a projection ray from the X-ray source to the detector. As a result, the correlation can be established between the regions of the object under examination that were penetrated by the beam, or rather the corresponding data of the ultrasound volume data set, and the projection position. However, geometrical information can also include yet more information, as will be explained in greater detail below.

The method according to an embodiment of the invention can be repeated for each region of interest of the object under examination, so that all the regions of interest of the object under examination can be viewed or diagnostically assessed in a simple manner.

For the abovementioned method for rendering a region of interest, a number of views are provided from a partial data set that has been determined according to a method according to the invention for determining a region to be rendered and at least one view is rendered.

The number of views can be one or more views which provide a (pseudo-)three-dimensional, preferably two-dimensional rendering of the partial data set. The number of views can therefore comprise, for example, a single two-dimensional image or a slice image stack of a plurality of images. The views can be provided time-independently of the rendering thereof by storing the views in a storage device, for example. Irrespective of whether they are generated directly or retrieved from a storage device, they can be shown on a normal display device such as a monitor, some another display, 3D glasses, a beamer or projector or similar.

An embodiment is directed to an image processing device incorporating all the components for carrying out one of the above described methods according to embodiments of the invention.

The image processing device can basically operate independently of the modalities required for acquisition. It can therefore be inventively used, for example, to also process data of separate X-ray and ultrasound equipment. Thus, for example, the location of a probe of the ultrasound device relative to the object under examination and/or X-ray unit can be determined/tracked by sensors using known methods. This also enables the relative location of the X-ray projection image and the three-dimensional ultrasound data set to be determined.

An embodiment is directed to an X-ray system comprising an inventive image processing device of at least one embodiment and an X-ray 3D ultrasound unit. The latter comprises a source-detector arrangement which is designed to acquire an X-ray projection image of an object under examination. The XUS unit also comprises an ultrasound arrangement which is designed to acquire an ultrasound volume data set. The XUS unit is preferably a mammography unit having an additional ultrasound arrangement as compared to standard mammography units.

The image processing device according to at least one embodiment of the invention can be advantageously retrofitted to existing X-ray systems. However, it is also possible to equip new X-ray systems with an image processing device according to at least one embodiment of the invention as early as the manufacturing stage thereof.

The essential components of the image processing device according to at least one embodiment of the invention can be largely implemented in the form of software components. However, especially when particularly rapid calculations are involved, some of these components can basically also be realized in the form of software-supported hardware, such as FPGAs or the like. Likewise, the required interfaces can be implemented as software interfaces, e.g. when only data transfer from other software components is involved. However, they can also be implemented as hardware-based interfaces which are controlled by suitable software.

In particular, the image processing device according to an embodiment of the invention can be part of a user terminal of an X-ray system.

An advantage of a largely software-based implementation is that even image processing equipment already in use can be easily upgraded by a software update in order to operate in the manner according to an embodiment of the invention. In this respect, at least one embodiment is directed to a corresponding computer program product comprising a computer program which can be loaded directly into a storage device of an image processing device of an X-ray system, having program sections for carrying out all the steps of the method according to an embodiment of the invention when the program is executed in the image processing device. As well as the computer program, such a computer program product can possibly comprise additional elements such as e.g. a documentation and/or additional components, including hardware components such as e.g. a hardware key (dongles, etc.) for using the software.

For transfer to the image processing device and/or to the storage device on or in the image processing device, a computer-readable medium, e.g. a memory stick, a hard disk or some other portable or built-in data carrier can be used on which the computer program sections readable and executable by a processing unit of the image processing device are stored. For this purpose the processing unit can have, for example, one or more interoperating microprocessors or the like.

Other particularly advantageous embodiments and further developments of the invention will emerge from the claims and the following description, wherein the independent claims of one claims category can also be further developed analogously to the dependent claims or description sections of another claim category and, in particular, individual features of different examples or variants can be combined to produce new examples or variants.

It is basically possible to delimit the region to be rendered by, for example, excluding edge areas located in the vicinity of the chest wall. The partial data set preferably comprises in particular at least all the partial data associated with regions of the object under examination which have been penetrated by the projection ray. The partial data set therefore comprises in particular all the information that is also accumulated in the image point of the projection position. That is to say, this includes at least the regions or rather sections of the ultrasound volume data set which are correlated to a line connecting the corresponding detector pixel to the X-ray source. This ensures that the diagnostician can find, even in the partial data set, at least the formation which he/she expects from the projection position determined. In addition, the partial data set can comprise yet more data, in particular from the region of interest, as will be explained in greater detail in the following.

In a first variant embodiment, the partial data set is preferably implemented as a surface. This surface is produced, for example, as an intersection of the ultrasound volume data set with a plane which represents, in the mathematical sense, a two-dimensional object of unlimited extent. The plane is defined using e.g. three vectors or rather the three-point form. A first vector, or more specifically a support vector, can be freely specified as an origin vector and is therefore fixed, for example, at a point (origin of the defined coordinate system) of a perpendicular projection of the X-ray source onto the detector. The plane can also be spanned, for example, by the following two support vectors:
- a first directional vector (U or z) perpendicular to the detector surface, i.e. in the direction from the origin to the X-ray source (or vice versa) and/or a directional vector (U or z) in a propagation direction, i.e. in a main propagation direction, of the ultrasound waves,
- a second directional vector (V) in the direction from the origin to the projection position.

Selecting the first directional vector in the propagation direction of the ultrasound waves is particularly advantageous, as it enables shadowing effects, i.e. acoustic shadowing, for example, that is produced by a lesion to be readily detected.

Because of the geometrical design, the projection ray also lies automatically in the above described plane. Via an intersection of the plane with the ultrasound volume data set, a two-dimensional partial data set is defined or rather extracted which also contains all the corresponding information in respect of the regions of the object under examination that have been penetrated by the projection ray. This surface can be provided and rendered in a simple manner as a two-dimensional view or image e.g. as part of the rendering method previously described.

In a second variant embodiment, the partial data set preferably comprises data from a defined volume region.

The volume region can be defined in a simple manner as the region having a distance of no more than 2 cm, preferably of no more than 1 cm, from the projection position in a direction perpendicular to the main propagation direction of the ultrasound waves.

The volume region preferably encompasses a corridor through the object under examination that extends in a first direction of the projection ray and has a corridor width of no more than 2 cm, with particular preference of no more than 1 cm. The statement that the corridor extends in a first direction of the projection ray means that its main extension direction is disposed in this direction. The first direction of the projection ray is preferably the component thereof that is perpendicular to a main propagation direction of the ultrasound waves. With particular preference, this component is at the same time parallel to the detector surface. The corridor width specifies the extent of the corridor in a direction perpendicular to the main extension direction which is preferably at the same time parallel to the detector surface and/or perpendicular to the main propagation direction of the ultrasound waves.

Alternatively, the volume region preferably encompasses an angular range. The apex of the angular range is disposed with particular preference at the position of the X-ray source. In the case of a conical geometry of the angular range, i.e. of the beam path emitted by the X-ray source, a conical ungula, for example, is produced as the intersection between the angular range and the ultrasound volume data set.

A three-dimensional partial data set is produced which also comprises at least the regions that are correlated to the projection ray. The region encompassed by the partial data set is greater in edge regions of the detector, i.e. greater the farther the projection position is from the X-ray source.

With particular preference, however, the partial data set comprises data of a bounding box of the ultrasound volume data set which completely encompasses, in particular exactly, the above described angular range. This advantageously facilitates the subsequent rendering.

As described above, the partial data set can be rendered, for example, as serially ordered slice images of a slice image stack, i.e. consecutive images ordered according to their position. The slice images can be disposed, for example parallel to the detector surface or e.g. perpendicular to the projection ray. In particular, the position or depth in the object under examination and the position in the slice image stack correspond.

The projection ray preferably constitutes a central axis of the angular range. That is to say, the angular range is disposed such that the projection ray extends in each case through the central point of an intersection with the angular range that is perpendicular to the latter. Such a central disposition of the projection ray partial data set ensures that the diagnostician can also include, in the diagnostic assessment, areas that are adjacent to the areas correlated to the projection ray.

The angular range preferably extends through angles of no more than 15°, with particular preference of no more than 10°, and with most particular preference of no more than 5°, with respect to the projection ray. As a result, in particular the edge areas of the detector where the radiation intensity and therefore the diagnostic quality in the X-ray projection image is lower can be examined over a wider area in the ultrasound volume data set or partial data set. This ensures a good diagnostic assessment in these regions also.

The partial data set preferably comprises partial data corresponding to a volume of no more than 3 $cm^3$, with particular preference of no more than 2 $cm^3$, with most particular preference of no more than 1 $cm^3$. This limiting of the partial data set ensures that the diagnostician does not need to assess a large stack of slice images. As a result, he/she can concentrate on the details in the region of interest.

The partial data set is preferably analyzed by automatic detection and/or automatic classification of the region of interest. For this purpose the partial data set can be transmitted e.g. to an integrated or also to an external CAD system. Using known CAD methods, an exact position of the region of interest is determined, i.e. the region of interest is pinpointed. Alternatively or in addition, classification is performed using known CAD methods. It is therefore advantageously determined whether it is the case of a benign or a malignant tissue change. If required, a more precise classification, i.e. classification of the tissue change, can possibly also take place.

The ultrasound volume data set and the two-dimensional X-ray projection image have preferably been acquired during a compression step, in particular a single compression step, of the object under examination. This avoids laborious mutual registration of the acquired data. It also saves examination time while reducing patient discomfort as well personnel and equipment costs.

The geometrical information preferably comprises at least one of the following items of information: beam geometry, distance between X-ray source and detector, thickness of the object under examination, distance between X-ray source and projection position.

The beam geometry describes the geometrical characteristics of the beam path of the X-ray source. Known geometries include parallel beam and cone beam, wherein cone-beam geometries are most frequently used in practice because of the simpler technical implementation. Other features used to characterize cone-beam geometry include the beam angle or emergent angle.

The distance between the X-ray source and the detector describes the shortest distance between the two components. Well known from practice are X-ray units where this distance, e.g. d, can be variably set via an adjustment device. In these cases the distance between the X-ray source and the detector must be ascertained. This can already be done, for example, as part of setting the adjustment device, i.e. via internal position determination and/or via a built-in stepping motor, for example, and/or via an additional distance meter, such as e.g. a laser distance meter.

Also the thickness of the object under examination corresponds to geometrical information relating to the XUS unit. It describes the extension of the object under examination in a direction perpendicular to the detector surface. The thickness of the object under examination can be determined, for example, via the distance between the detector and a compression plate that can be lowered thereunto, i.e. moved toward and away from the detector. This distance can be ascertained by the devices/methods described above.

Alternatively or in addition, the thickness of the object under examination can also be determined from the ultrasound volume data set. If the position of the projection ray is known, it can be used to determine an entry/exit point to/from the object under examination and consequently also the regions penetrated in the object under examination.

The distance between the X-ray source and the projection position corresponds, as already described above, to the distance between the X-ray source and the detector pixel which is associated with the image point of the projection position. This distance can be easily determined if the distance from the X-ray source to the detector and the dimensions of the detector itself are known. With particular preference, the location of the projection position relative to the X-ray source is determined. This makes it possible to reconstruct the course of the projection ray as a connecting line between the projection position or rather the responding detector pixel and the X-ray source.

The projection position is preferably determined manually and/or automatically. That is to say, the projection position can be input by a user or diagnostician by, for example, clicking on a corresponding image point in the X-ray projection image displayed, entering image point coordinates or similar. Additionally or alternatively, the projection position can be determined automatically via a CAD algorithm (computer aided detection). Well known from practice are a large number of such algorithms which use, for example, methods such as thresholding, edge detection and/or similar.

In combination, the determination can take place, for example, by the operator inputting a region in which automatic determination is then to take place. Conversely, as part of a CAD algorithm, a region can first be determined in which the projection position is then specified by the operator. In addition, it is also possible, via the CAD algorithm, to suggest a projection position which can then be corrected by the operator if necessary.

Altogether at least one embodiment the invention makes it possible to reduce a relatively large ultrasound volume data set for diagnostic assessment to a small partial data set by using the X-ray projection image as an overview or more specifically for selecting the region of interest or rather the projection position. This allows faster yet thorough diagnostic assessment, wherein the diagnostician is only confronted by the kinds of image material with which he is already familiar from his daily profession practice. Moreover, the X-ray dose for the patient is advantageously minimized, as only one X-ray projection image needs to be prepared as a scout view.

FIG. 1 shows by way of example and in grossly schematic form an X-ray system 1 according to an embodiment of the invention, here a mammography system. Relative directional information such as "above" and "below", etc. relate to a mammography system 1 properly set up for operation. The mammography system 1 comprises a combined X-ray/ultrasound unit 2 (XUS unit), here a mammography ultrasound unit, and a computer system 20. The XUS unit 2 has a support column 17 and source-detector arrangement 3 which in turn comprises an X-ray source Q and a detector 5 having a detection surface D. The support column 17 stands on the underlying surface during operation. The source-detector arrangement 3 is movably connected thereto so that the height of the detector surface D, i.e. the distance from the underlying surface, can be adjusted to a patient's breast height.

The patient's breast B (schematically represented here) lies on top of the detector surface D as the object under examination B. Disposed above the breast B and the detector surface D is an ultrasound arrangement 6 which at the same time serves as a compression plate and is movably connected to the source-detector arrangement 3. For the examination, the breast B is compressed and simultaneously fixed in position by lowering the ultrasound arrangement 6 onto it so that pressure is applied to the breast O between ultrasound arrangement 6 and detector surface D.

The X-ray source Q is disposed facing the detector 5 and designed such that the detector 5 detects the X-radiation emitted thereby after at least some of the X-radiation has penetrated the patient's breast O. An X-ray projection image is thus obtained. The source-detector arrangement 3 can be swiveled relative to the support column 17 via a rotating arm 18 through a range of e.g. ±90 about a home position in which it is perpendicular to the underlying surface. By swiveling the source-detector arrangement 3, data for the breast B can be acquired from different body directions of the patient, i.e. cranio-caudal, medio-lateral, medio-lateral-oblique, for example, or the like.

The ultrasound arrangement 6 comprises an ultrasound probe (not shown here) which emits ultrasound waves in the direction of the breast B during operation. The ultrasound waves are scattered, refracted and reflected from the different structures of the breast B. The returning ultrasound waves are received again by the ultrasound probe and then evaluated and converted so that a three-dimensional ultrasound volume data set 3D-US of the inside of the breast B can be produced.

The computer system 20 comprises a processing unit 12 and, connected thereto, a mouse 13, a keyboard 14 and a screen 15. The screen 15 is used here as a display unit 15, the mouse 13 and keyboard 14 as input devices. The processing unit 12 comprises an image processing device 10 and a rendering device 11 (here schematically represented as blocks) and a disk drive 16 for reading in CDs or DVDs. The image processing device 10 and the rendering device 11 can share components of the processing unit 12, such as e.g. memory, processors and the like. The computer system 20 can be disposed in the same room as the XUS unit 2, but can also be located in an adjacent control room or at an even more remote location.

FIG. 2 shows an example embodiment of a processing device according to an embodiment of the invention 10 together with an example embodiment of a rendering device 11. The image processing device 10 comprises an input interface 21 and an output interface 22 as well as a determination unit 23 and an extraction unit 24. The input interface 21 is connected to the determination unit 23 and transmits incoming data comprising a three-dimensional ultrasound volume data set 3D-US, an X-ray projection image RB and geometrical information GI to the determination unit 23.

Figure 5:
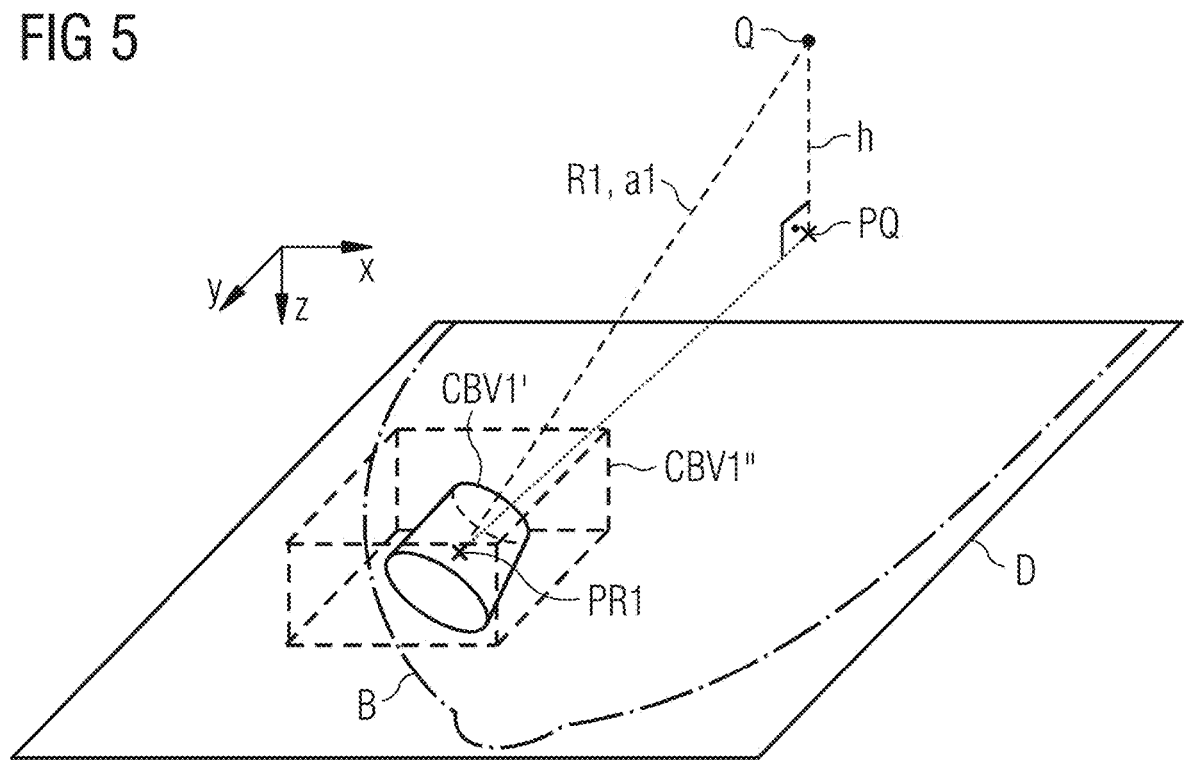
FIG. 5 shows a schematic perspective view of the extraction of a partial data set according to a second example embodiment of a method according to the invention for determining a region of interest to be rendered.

A projection position PR1, PR2 is determined from the X-ray projection image RB e.g. via a user input BE (see FIGS. 4 and 5). The projection position PR1, PR2 determined together with the ultrasound volume data set 3D-US and geometrical information GI is transmitted to the extraction unit 24. There a partial data set CBV1, CBV1', CBV2 is extracted from the ultrasound volume data set 3D-US on the basis of the projection position PR1, PR2 and geometrical information GI, as will be explained in greater detail with reference to FIGS. 3 to 5. The partial data set CBV1, CBV1', CBV2 is forwarded to the rendering device 11 via the output interface 22.

The rendering device 11 comprises a provisioning unit 25 and a rendering unit 26. The provisioning unit 25 selects from the partial data set CBV1, CBV1', CBV2 a number of views in which the region of interest can be best rendered for a diagnostician. These views are processed by the rendering unit 26 such that they can be shown on a usual display unit such as the screen 15, for example.

FIG. 3 shows in grossly schematic from a block diagram representing, in two steps IV and V, the sequence of an example embodiment of a method according to the invention for determining a region of interest to be rendered and, in two steps VI and VII, the sequence of an example embodiment of a method according to the invention for rendering a region of interest.

In a preparatory first step I, which is not part of the method according to an embodiment of the invention, the patient's breast B is compressed between the detector 5 and the ultrasound arrangement 6 by lowering the ultrasound arrangement 6 onto the detector 5 until a predefined pressure is exerted on the breast B. In the compressed state, the breast B can be better examined both via X-rays and via ultrasound and is also fixed in position such that no positioning of the breast B takes place between the individual acquisition steps described in the following.

In a preparatory second step II, which is likewise not part of the method according to an embodiment of the invention, an X-ray projection image RB is acquired. As already described in the introduction, an X-ray source Q is used to produce X-radiation which penetrates the breast B and is then incident in attenuated form on the detector surface D and is detected as a function of the intensity thereof. The attenuation or rather absorption, i.e. the reduction in the detected intensity, of the X-radiation is dependent on the structures or density of the irradiated tissue of the breast B. The acquired X-ray projection image RB can be displayed on the screen 15, for example.

In a preparatory step III which is likewise not part of the method according to an embodiment of the invention, a three-dimensional ultrasound volume data set 3D-US is acquired. For this purpose, ultrasound waves in the form of ultrasound pulses at different positions in relation to the breast B are emitted in a scan-like manner according to a method well known to persons skilled in the art. These are scattered, refracted and reflected from different structures of the object under examination. The returning ultrasound waves are received again by the ultrasound probe and then evaluated and converted into the three-dimensional ultrasound volume data set 3D-US.

Steps II and III can basically be carried out time-independently of one another as long as transmission of the x-radiation by the ultrasound arrangement 6 is ensured. However, the X-ray projection image RB is preferably acquired prior to acquisition of the ultrasound volume data set 3D-US, as this enables a subsequent fourth step IV to be already carried out in parallel.

The fourth step IV begins the actual example embodiment of the method according to an embodiment of the invention for determining a region of interest to be rendered, the steps of which will be described in further detail with reference to FIGS. 4 and 5. The fourth step IV describes determination of a projection position PR1, PR2. The determination can take place, for example, via a manual input by a user BE. In addition or alternatively for the determination, a CAD algorithm can be executed which automatically detects the region of interest and possibly also the projection position PR1, PR2 using known methods. The projection position PR1, PR2 corresponds to a point on the detector surface D.

In a fifth step V, a partial data set CBV1, CBV1', CBV1'' CBV2 is extracted from the ultrasound volume data set 3D-US. This is done on the basis of the projection position PR1, PR2 and geometrical information GI relating to the XUS unit 2, as will be explained in the following using two examples with reference to FIG. 4 and FIG. 5.

FIG. 4 shows by way of example a schematic perspective representation to illustrate the extraction of two partial data sets CBV1, CBV2. The X-ray source Q is disposed at a perpendicular distance, i.e. a height h, above the detector surface D. The detector 5 is a plurality of pixels which are arranged in the manner of a matrix in the detection surface D. The pixels are organized into rows and columns perpendicular to one another which extend in the main directions of the detector 5 (not shown here for the sake of better representation). An outline of the breast B is shown on the detector surface D by way of illustration. To facilitate orientation, a right-handed Cartesian coordinate system having an x-direction, a y-direction and a z-direction is also shown. The z-direction corresponds to a direction from the X-ray source Q to a projection point of the X-ray source Q on the detector surface D. The y-direction corresponds to a main direction of the detector 5 which essentially points away from the patient, and the x-direction, which corresponds to the other main direction of the detector 5, results from adding the two preceding directions to form a right-handed Cartesian coordinate system.

The first projection position PR1 determined in the fourth step IV corresponds to a position or rather a pixel of the detector surface D. A first projection ray R1 extends from the X-ray source Q up to the first projection position PR1. A length of the first projection ray R1 corresponds to the distance a1 between the X-ray source Q and the projection position PR1. The location of the first projection ray R1 in relation to the ultrasound volume data set 3D-US can be assigned using the geometrical information GI. That is to say, the location of the first projection ray R1 relative to the detector surface D and the X-ray source Q can be determined, as the location of the X-ray source Q relative to the detector surface D is also known or can at least be determined. For this purpose the positions of the X-ray source Q and the detector surface D, for example, can be described in a common coordinate system (x, y, z).

The first partial data set CBV1 associated with the projection position PR1 can be selected from the ultrasound volume data set 3D-US as follows. First a plane is constructed which is spanned by a first directional vector U1 and a second directional vector V1. The first directional vector U1 extends in a direction from the projection point PQ of the X-ray source Q to the first projection position PR1. The second directional vector V1 here extends (for better representation and without limitation of generality) in an opposite direction to the z-direction (the second direction vector V1 can likewise also simply extend in the z-direction). The first partial data set CBV1 (here shown only schematically and in part) is consequently formed from an intersection between the above described plane and the ultrasound volume data set 3D-US. Because of its construction, the partial data set in any case comprises the data corresponding to the regions penetrated by the projection ray R1. It is also possible to additionally reduce the first partial data set CBV1 by extracting only a defined region of the intersection and one which is sufficient for diagnostic assessment, the region encompassing the projection position, preferably centrally.

For the second projection position PR2, for further illustration, a construction for the extraction of the second partial data set CBV2 is shown which can be understood analogously to the explanations just given in respect of the first partial data set CBV1.

FIG. 5 shows by way of example a schematic perspective representation to illustrate the extraction of two partial data sets CBV1', CBV1''. FIG. 5 is essentially similar to FIG. 4, for which reason only the different extraction of the partial data sets CBV1', CBV1'' will be explained in greater detail in the following.

Analogously to FIG. 4, the location of the projection ray R1 in relation to the ultrasound volume data set is known. However, to select the third partial data set CBV1', instead of a plane, a truncated cone is now constructed. The truncated cone represents the conical beam characteristics or rather beam geometry of the X-ray source Q. It has an imaginary apex, a central axis and an aperture angle. The imaginary apex is disposed at the same position as the X-ray source Q. The central axis extends in a direction of the projection ray R1 through central points of cross-sectional areas of the truncated cone that are perpendicular thereto. The aperture angle denotes an aperture angle of the cone for which the central axis is a bisector. It is here e.g. 10°. The projection position P1 is disposed centrally in the truncated cone. That is to say, the truncated cone extends in the direction of the projection ray and oppositely to both sides of the projection position PR1 in a defined region. The third partial data set CBV1' is formed from an intersection of the thus constructed truncated cone and the ultrasound volume data set 3D-US.

For simpler rendering of the third partial data set CBV1', additional data from adjacent regions of the ultrasound volume data set 3D-US can be used. A fourth partial data set CBV1'' is accordingly extracted which encompasses the third partial data set CBV1', preferably as a bounding box, in a defined region of the ultrasound volume data set 3D-US larger than the truncated cone. The fourth partial data set CBV1'' is preferably arranged such that its main extension directions correspond to the x-y-z-directions of the Cartesian coordinate system described above.

The above-described defined regions for the partial data sets CBV1', CBV1'' are preferably specified such that they correspond to a volume of no more than 3 $cm^3$, preferably of no more than 2 $cm^3$, with particular preference of no more than 1 $cm^3$.

The partial data sets CBV1, CBV1', CBV1'', CBV2 are also characterized as cone beam views and can be stored separately. They constitute a more quickly assessable sub-set of the ultrasound volume data set 3D-US.

Concerning FIGS. 4 and 5, it should be noted that they are by no means drawn to scale. Thus, the height h of the X-ray source Q above the detector surface D is usually much greater than that shown here. The arrangement has also been simplified for ease of representation. Unlike the arrangement shown, the X-ray source Q is preferably disposed as centrally as possible above the detector surface D.

The partial data sets CBV1, CBV1', CBV1'', CBV2 extracted in this manner are rendered in the following steps VI and VII now described again with reference to FIG. 3 according to an example embodiment of a method according to the invention for rendering a region of interest. For this purpose, a number of views are first provided in a sixth step VI. They can be provided, for example, by receiving views directly from the image processing unit or by retrieving them from a storage device. In the case of the partial data sets CBV1, CBV2, another region to be displayed can be selected as a two dimensional image, for example. In the case of the partial data sets CBV1', CBV1'', e.g. another viewing direction onto the three-dimensional volume data set can be specified and corresponding views generated.

If e.g. in the case of the partial data sets CBV1', CBV1'' a plurality of views 30 are present, in a step VII one or more (with simultaneous rendering) of the views 30 are selected for display. Thus, as the first per se, for example, a view 30 is selected which includes the projection position. Further views can be rendered, for example, as a consecutive sequence, e.g. images ordered according to depth, in particular as a film or controlled by user inputs such as scrolling or the like.

The single rendering takes place in an eighth step VIII by transmitting the number of views 30 to be rendered to a display unit, such as the screen 15, for example.

Figure 6:
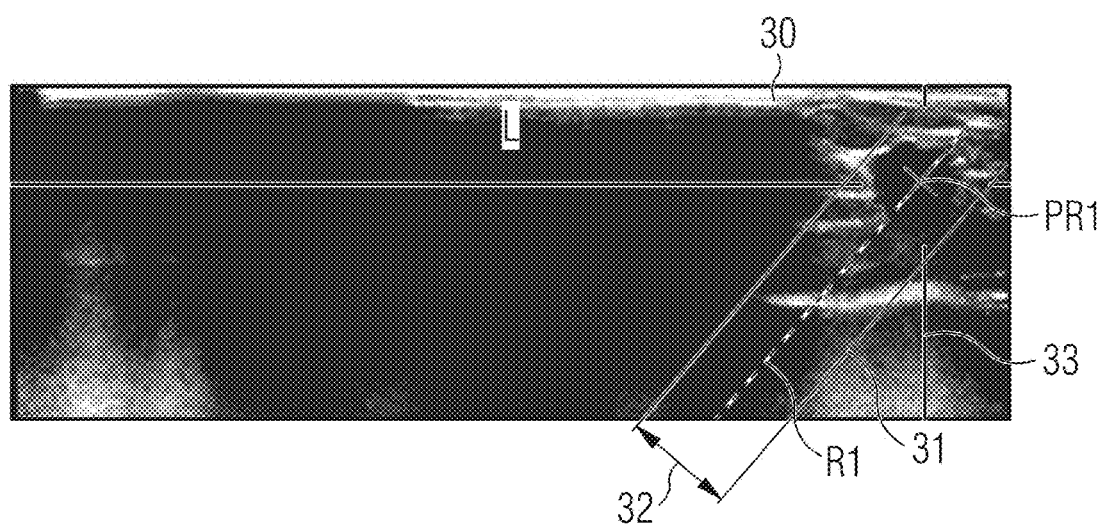
FIG. 6 shows a view which was determined from an ultrasound volume data set by way of an example embodiment of a method according to the invention for rendering a region of interest.

Such a view 30 is shown by way of example in FIG. 6. In a region of interest of the object under examination B, in the X-ray projection image RB the projection position PR1 has been determined which is also visualized in the view 30 of an inventively determined partial data set via a crosshair 33. The location of the projection ray R1 relative to the view 30 is also marked. The partial data set comprises at least the data of the ultrasound volume data set 3D-UV which originates from a corridor 31 of the object under examination B. The corridor 31 extends in the plane of the view 30 (which is essentially disposed perpendicular to the main propagation direction of the ultrasound waves) and parallel to the projection ray R1. The corridor has a corridor width 32 of 2 cm.

The present invention therefore allows simple, fast diagnostic assessment, as the region of interest is pre-selected in the X-ray projection image instead of the entire ultrasound volume data set having to be considered. As only one X-ray projection image needs to be acquired as an overview, the radiation exposure of the patient is advantageously low.

In conclusion, it is once again pointed out that the devices and methods described in detail above are merely examples which can be modified in a wide variety of ways by persons skilled in the art without departing from the scope of the invention. Although only a mammography system has been described above by way of example, the invention can basically relate to any X-ray system with combined X-ray 3D ultrasound unit. In addition, the use of the indefinite article "a" or "an" does not exclude the possibility of a plurality of the features in question also being present. Likewise, the terms "device", "arrangement" and "system" do not exclude the possibility that the components in question consist of a plurality of interoperating sub-components that may possibly also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a region of interest to be rendered in an ultrasound volume data set of an interior of an object under examination, the data set having been acquired via an X-ray three dimensional (3D) ultrasound unit, the method comprising:
   determining a projection position in a two dimensional X-ray projection image of the object under examination, wherein a projection ray correlated to the projection position passes through the region of interest; and
   extracting a partial data set encompassed by the ultrasound volume data set using the projection position determined and based upon geometrical information relating to the X-ray 3D ultrasound unit.

2. The method of claim 1, wherein the partial data set at least includes partial data, correlated to regions of the object under examination penetrated by the projection ray.

3. The method of claim 2, wherein the partial data set is implemented as a surface.

4. The method of claim 2, wherein the partial data set includes data from a defined volume range.

5. The method of claim 4, wherein the volume range encompasses a corridor through the object under examination extending in a first direction of the projection ray and includes a corridor width of no more than 2 cm.

6. The method of claim 1, wherein the partial data set includes data from a defined volume range.

7. The method of claim 6, wherein the volume range encompasses a corridor through the object under examination extending in a first direction of the projection ray and includes a corridor width of no more than 2 cm.

8. The method of claim 7, wherein the volume range includes a corridor width of no more than 1 cm.

9. The method of claim 7, wherein the partial data set includes partial data corresponding to a volume of no more than 3 cm$^3$.

10. The method of claim 6, wherein the partial data set includes partial data corresponding to a volume of no more than 3 cm$^3$.

11. The method of claim 10, wherein the partial data set includes partial data corresponding to a volume of no more than 2 cm$^3$.

12. The method of claim 11, wherein the partial data set includes partial data corresponding to a volume of no more than 1 cm$^3$.

13. The method of claim 1, wherein the partial data set is analyzed via at least one of automatic detection and automatic classification of the region of interest.

14. The method of claim 1, wherein the ultrasound volume data set and the two dimensional X-ray projection image have been acquired during a compression step of the object under examination.

15. The method of claim 1, wherein the geometrical information includes at least one of: beam geometry, distance between X-ray source and detector, thickness of the object under examination, and distance between X-ray source and projection position.

16. The method of claim 1, wherein the projection position is determined at least one of manually and automatically.

17. A method for rendering a region of interest, comprising:
   providing a number of views from a partial data set determined according to the method of claim 1; and
   rendering at least one view of the number of views provided.

18. A non-transitory computer program product storing a computer program, directly loadable into a storage device of an image processing device, including program sections for carrying out the method of claim 1 when the computer program is executed in the image processing device.

19. A non-transitory computer-readable medium storing program sections readable and executable by a processor to carry out the method of claim 1 when the program sections are executed by the processor.

20. An image processing device for determining a region of interest to be rendered in an ultrasound volume data set of an inside of an object under examination, the data set having been acquired via an X-ray 3D ultrasound unit, the image processing device comprising:
   at least one processor to
      determine a projection position in a two dimensional X-ray projection image of the object under examination, wherein a projection ray correlated to the projection position passes through the region of interest and
      extract a partial data set from the ultrasound volume data set using the projection position determined and based upon geometrical information relating to the X-ray 3D ultrasound unit.

21. An X-ray system, comprising:
   the image processing device of claim 20; and
   an X-ray 3D ultrasound unit including
      a source-detector arrangement designed to obtain an X-ray projection image of an object under examination, and an ultrasound arrangement designed to acquire an ultrasound volume data set.

* * * * *